United States Patent
Birecki et al.

(10) Patent No.: US 7,386,333 B1
(45) Date of Patent: Jun. 10, 2008

(54) TEST SUBJECT MONITORING DEVICE

(76) Inventors: Henryk Birecki, 1501 Page Mill Rd., Palo Alto, CA (US) 94304; Manish Sharma, 1501 Page Mill Rd., Sunnyvale, CA (US) 94304; James A. Brug, 1501 Page Mill Rd., Menlo Park, CA (US) 94304

( * ) Notice: Subject to any disclaimer, the term of this patent is extended or adjusted under 35 U.S.C. 154(b) by 497 days.

(21) Appl. No.: 11/117,974

(22) Filed: Apr. 29, 2005

(51) Int. Cl.
*A61B 5/1455* (2006.01)
(52) U.S. Cl. .................................. 600/310; 600/322
(58) Field of Classification Search ............... 600/310, 600/317, 322, 323
See application file for complete search history.

(56) References Cited

U.S. PATENT DOCUMENTS

| | | | |
|---|---|---|---|
| 4,779,173 A | 10/1988 | Carr et al. | |
| 5,172,693 A * | 12/1992 | Doody | 600/317 |
| 5,335,305 A | 8/1994 | Kosa et al. | |
| 5,630,413 A * | 5/1997 | Thomas et al. | 600/310 |
| 5,684,296 A | 11/1997 | Hamblin et al. | |
| 6,029,304 A | 2/2000 | Hulke et al. | |
| 6,415,167 B1 * | 7/2002 | Blank et al. | 600/344 |
| 6,560,470 B1 * | 5/2003 | Pologe | 600/310 |
| 6,623,698 B2 | 9/2003 | Kuo | |
| 2004/0215134 A1 * | 10/2004 | Soykan et al. | 604/66 |
| 2004/0220498 A1 | 11/2004 | Li et al. | |

OTHER PUBLICATIONS

Gouma, P. et al., "Novel Material and Application of Electronic Noses and Tongues", MRS Bullentin, Oct. 2004, www.mrs.org/publications/bulletin.
"10 Technologies On Top", Future Watch, Issue Mar. 2001, Aug. 2001.
www.darpa.mil/dso/trans/pdf/Abmt2.pdf, dowloaded Apr. 29, 2005.
www.salimetrics.com, dowloaded Apr. 29, 2005.
www.specs.com/products/Kamina/chemical-gas-sensor.PDF., dowloaded Apr. 29, 2005.

* cited by examiner

*Primary Examiner*—Eric F. Winakur
*Assistant Examiner*—Etsub D Berhanu

(57) ABSTRACT

A device for monitoring a test subject includes a light source and at least one optical waveguide configured for at least one of directing light from the light source onto a biological substrate and receiving the light directed onto the biological substrate. The device also includes a sensor operable to detect the light received, a logic component operable to analyze the light detected by the sensor, an output component operable to convey information from the logic component to a user of the device, and a housing containing the light source, the sensor, the logic component, and the output component, where the at least one optical waveguide forms at least one bristle extending outside of the housing.

25 Claims, 8 Drawing Sheets

TEST SUBJECT MONITORING DEVICE

BACKGROUND

Personal healthcare typically requires invasive testing and monitoring. A person typically goes to a hospital, clinical laboratory, or doctor's office and undergoes one or more clinical tests that involve invasive testing to determine the person's wellbeing and general health. Conventional clinical tests during physical examination often involve the taking of a blood sample to test for a range of medical conditions. Taking a blond sample usually necessitates the insertion of a needle or other instrument which is often a painful experience. Physical examination often necessitate other types of invasive testing and monitoring.

In addition to the inconvenience and costs associated with invasive testing in a hospital or clinical laboratory setting, most people only very infrequently undergo such invasive testing. Such infrequent or intermittent testing often poses risks to a person's health, because one or more signs or symptoms of a potential illness or disease are often overlooked or detected too late because the testing was not performed sufficiently early. In addition, it is difficult to maintain a preventive approach to healthcare because of the infrequent or intermittent testing and monitoring that occurs. More frequent monitoring and testing is necessary in order to maintain a more accurate record of the person's health.

Moreover, the costs associated with physical examinations and clinical testing often deter people from seeking healthcare. Additional laboratory testing typically adds significant costs to the burden associated with a physical examination. A relatively simple and inexpensive device capable of monitoring and testing would therefore be beneficial.

SUMMARY

A device for monitoring a test subject is disclosed herein. The device includes a light source and at least one optical waveguide configured for at least one of directing light from the light source onto a biological substrate and receiving the light directed onto the biological substrate. The device also includes a sensor operable to detect the light received, a logic component operable to analyze the light detected by the senor, an output component operable to convey information from the logic component to a user of the device, and a housing containing the light source, the sensor, the logic component, and the output component, where the at least one optical waveguide forms at least one bristle extending outside of the housing.

BRIEF DESCRIPTION OF THE DRAWINGS

Embodiments are illustrated by way of example and not limitation in the accompanying figures in which like numeral references refer to like elements, and wherein.

DETAILED DESCRIPTION

For simplicity and illustrative purposes, the principles of the embodiments are described. However, one of ordinary skill in the art would readily recognize that the same principles are equally applicable to, and can be implemented with variations that do not depart from the true spirit and scope of the embodiments. Moreover, in the following detailed description, references are made to the accompanying figures, which illustrate specific embodiments.

Figure 1:
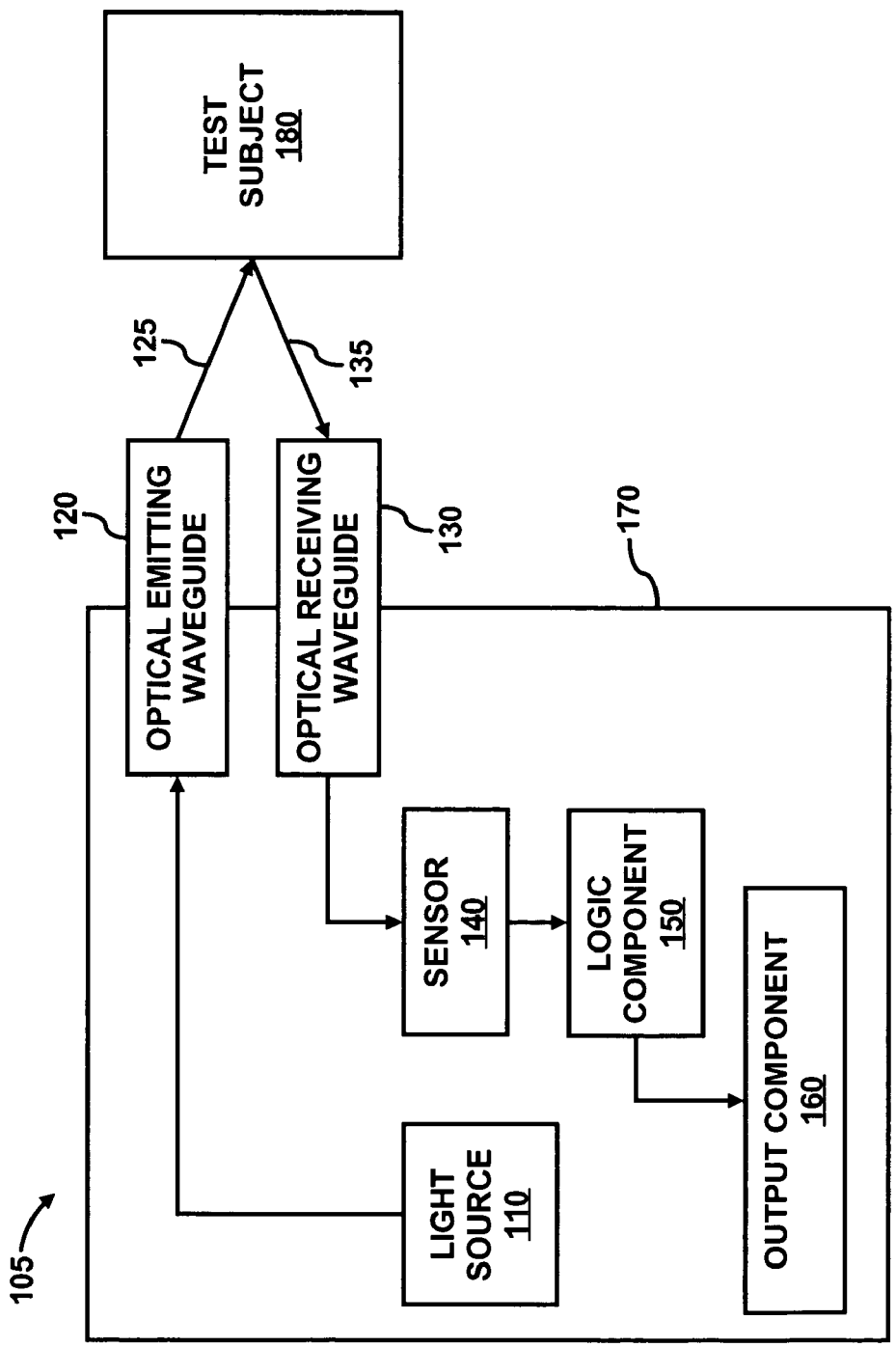
FIG. 1 shows a system for monitoring a test subject, according to an embodiment.

Referring to FIG. 1, there is shown a device 105 for monitoring a test subject 180. The device 105 may comprise a mobile device, such as a handheld device, or a stationary device. The device 105 may be fabricated to have a suitable size for handheld use, such as a size on the order of several inches or centimeters in each dimension. The device 105 may also be fabricated to have a suitable size as a stationary device, for instance, on the order of several inches or centimeters in each dimension.

The test subject 180 may include a person or animal. In addition, the test subject 180 may includes an anatomic feature of a person or animal, such as the skin, the inner ear, a mucosal lining, or another feature of the subject's body. In addition, the test subject 180 may include a biological substrate of the person or animal, such as a sample of blood or saliva obtained from the person or animal.

The device 105 includes a light source 110. The light source 110 may include an internal power source (not shown), such as a battery, or may alternatively include a rechargeable power source which derives power from connection to a charger. The light source 110 may also include a meter, such as a potentiometer (not shown), for adjusting the light intensity as desired or needed. For instance, the light source 110 may include a meter operable to produce light of a suitable intensity and wavelength for use in monitoring the test subject 180. In addition, the light source 110 may be fabricated to include a light emitting diode (LED) that produces or emits light when connected in a circuit. The light source 110 may also include other circuitry or components (not shown) for producing light.

The device 105 may include at least one optical waveguide 120, 130 configured for at least one of directing light 125 from the light source 110 onto the test subject 180 and receiving light 135 directed onto the test subject 180. Thus, at least one optical waveguide 120, 130 may be provided which operates both as a light input guide and as a light output guide. One example of an optical waveguide which operates both as a light input guide and a light output guide is discussed below, with reference to the optical waveguide 285 shown in FIG. 2B.

Alternatively, the device 105 may include at least one optical emitting waveguide 120 and at least one optical receiving waveguide 130, as described in detail below. The device 105 may thus include at least one optical emitting waveguide 120 operable to direct light 125 from the light source 110 onto the test subject 180, or onto a biological substrate of the test subject 180. The optical emitting waveguide 120 may be fabricated as a light guide, fiber optic, bristle waveguide, light pipe, or other suitable structure operable to direct light 125 from the light source 110 onto the test subject 180. The optical emitting waveguide 120 may also be fabricated to have a suitable length, width or other dimensions as needed or desired.

The device 105 also includes at least one optical receiving waveguide 130 operable to receive or guide light 135 back from the test subject 180, or back from a biological substrate of the test subject 180. The optical receiving waveguide 130 may also be fabricated as a light guide, fiber optic, bristle waveguide, light pipe, or other suitable structure operable to receive or guide light 135 back from the test subject 180, or back from a biological substrate of the test subject 180. In addition, the optical receiving waveguide 130 may be fabricated to have a suitable length, width or other dimensions as needed or desired.

The optical receiving waveguide 130 is further operable to receive or guide light 135 back from the test subject 280, or back from a biological substrate of the test subject 180, and transmit the light 135 to a sensor 140.

The sensor 140 is operable to detect the light 135 received by the optical receiving waveguide 130. The sensor 140 may include, for instance, at least one of a photodiode, a charge-coupled device (CCD), a photodetector, or other photosensitive element operable to detect the light 135 received by the optical receiving waveguide 130. In addition, the sensor 140 may detect the intensity of the light 135 and may also analyze the spectral content of the light 135. For instance, the sensor 140 may analyze the spectral content of the light 135 using one or more of a grating, a prism, an interferometer, another suitable interference device, a spectrometer, and the like. A Fabry-Perot spectrum analyzer (not explicitly shown) may also be used to analyze the spectral content of the light 135.

The device 105 further includes a logic component 150 operable to analyze the light 135 detected by the sensor 140. The logic component 150 may include circuitry operable to analyze, for instance, fluorescence of the light 135. The logic component 150 may, for instance, also include circuitry operable to perform one or more logic or arithmetic functions for analyzing the fluorescence and intensity of the light 135 detected by the sensor 140.

The device 105 also includes an output component 160 operable to convey information from the logic component 150 to a user, such as a user of the device 105. The output component 160 may include at least one of a visual display and an audible component operable to convey the information to the user. In addition to the output component 160, the device 105 also includes a housing 170. The housing 170 may be fabricated to contain the light source 110, the sensor 140, the logic component 150, and the output component 160. In addition, the housing 170 may be fabricated out of a synthetic material, such as a plastic or a polymer. The housing 170 may also be fabricated out of a composite of one or more polymers, synthetic materials or alloys. In addition, the optical emitting waveguide 120 and the optical receiving waveguide 130 may each extend from a location inside of the housing 170 to a location outside of the housing 170.

Figure 2A:
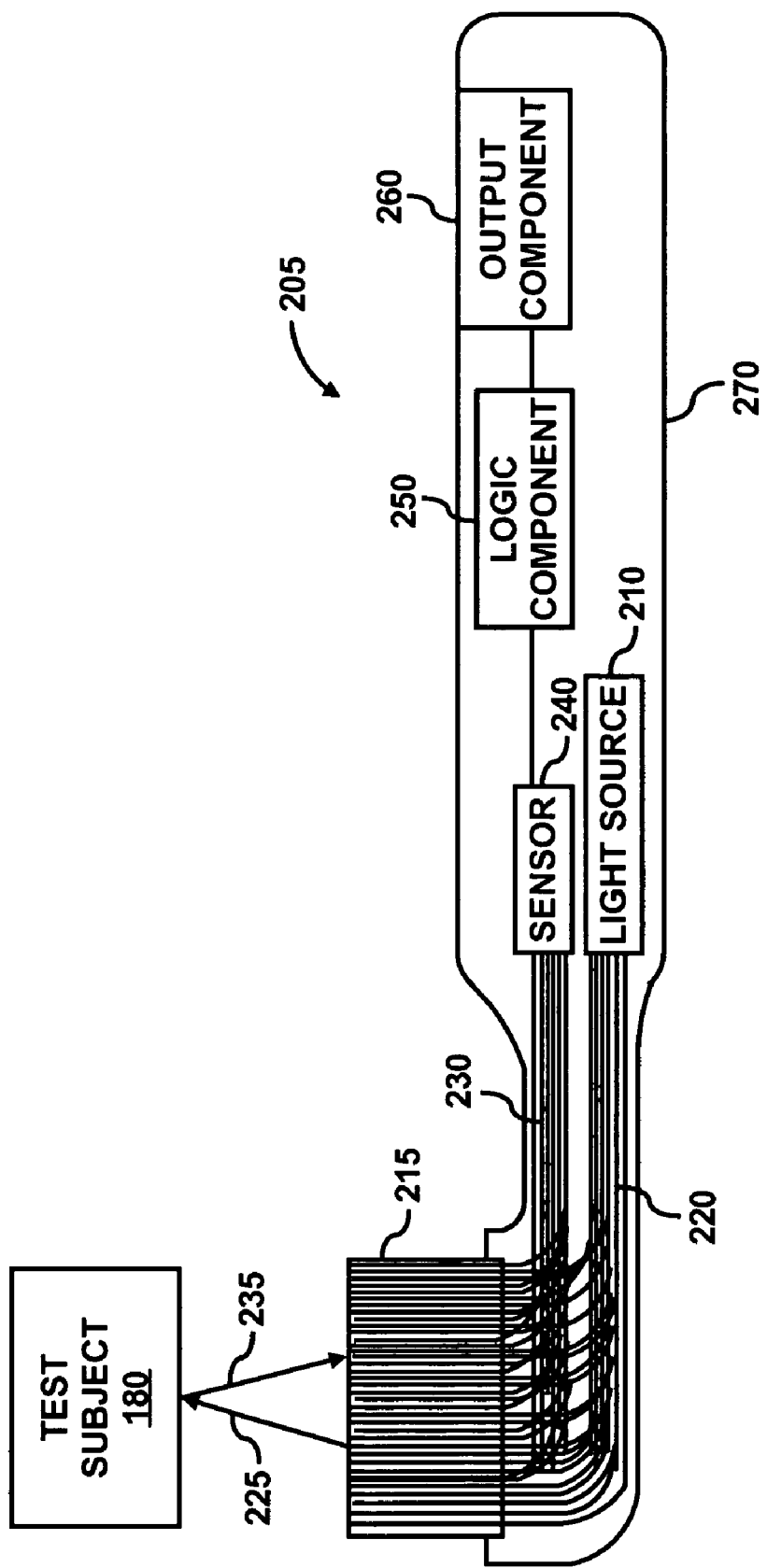
FIG. 2A shows a device for monitoring a test subject, where the device comprises at least one optical emitting waveguide and at least one optical receiving waveguide, according to an embodiment.

Referring to FIG. 2A, there is shown a device 205 for monitoring the test subject 180. The device 205 is one, more detailed, example of the device 105 shown in FIG. 1. As shown, the device 205 generally comprises a toothbrush 205, which includes various components for monitoring the test subject 180. According to one example, the toothbrush 205 may include a toothbrush operable to be held and used by a person for monitoring the health of the person's teeth, gums, and other parts of a person's mouth. The toothbrush 205 may thus be used by a person for maintaining oral hygiene and, in addition, for monitoring the person's health as described in further detail below.

The toothbrush 205 may be fabricated to have a suitable size for handheld use, such as a size on the order of several inches or centimeters in each dimension. In addition, although the toothbrush 205 is shown in FIG. 2A as having a particular shape, the toothbrush 205 may also be fabricated to have another suitable shape, for instance, with substantially curved edges, or with substantially straight edges, or having another reasonably suitable shape.

The toothbrush 205 may be used, for instance, as an optical imaging tool for imaging the subject's mouth, and thus may be used for cavity detection, monitoring for gum disease, or monitoring of other potential problems associated with the subject's health. In addition, the test subject 180 may include a biological substrate of the subject, such as a sample of blood or saliva obtained from the subject, as described in further detail below.

The toothbrush 205 includes a light source 210, for instance, a light emitting diode (LED) for emitting a beam of light for subsequent emission by an optical emitting waveguide 220. The optical emitting waveguide 220 may be formed as one of a plurality of bristles, or bristle waveguides 215. Some or all of the bristle waveguides 215 may thus operate as a structure for transmitting light. For instance, each of the bristle waveguides 215 may be constructed as a fiber optic, an optical waveguide, or a light guide operable to transmit light through the interior of each respective bristle waveguide 215.

Each of the bristle waveguides 215 may be hollow or substantially hollow, and thus each may form a capillary structure. These hollow or substantially hollow bristle waveguides 215 may also have surfaces that are coated with one or more analyte compounds. An analyte compound may include a compound or a substance from the test subject 180 that may be identified with the toothbrush 205 using a biochemical assay or diagnostic test. One or more analyte compounds may thus be identified from a saliva or blood sample from the test subject 180 using one or more tests, such as one or more diagnostic tests or assays. For instance, when the toothbrush 205 is used by a user, one or more of the bristle waveguides 215 may fill with saliva due to capillary action. The saliva may thus be drawn through one or more of the bristle waveguides 215. A separate detector (not explicitly shown) may be used to detect and analyze the saliva or blood sample present in the bristle waveguides 215.

In addition, a separate light source (not explicitly shown) may be used to project light upon the bristle waveguides 215. The hollow or substantially hollow bristle waveguides 215 may be formed from a substantially transparent or translucent material, thus allowing the light to be transmitted through the bristle waveguides 215. An optical detector may also be used to detect the percentage or intensity of the light that is transmitted through the bristle waveguides 215. The presence of saliva or another substance in the bristle waveguides 215 may change the percentage or intensity of light transmitted through the bristle waveguides 215, and thus the percentage or intensity of light detected by the optical detector. The bristle waveguides 215 may be formed in addition to other bristles for use with the toothbrush 205.

The light source 210 may also be powered by an internal power source (not shown), such as a battery, or may alternatively receive power from a rechargeable power source which derives power from connection to a charger. In addition, the light source 210 may include a meter (not shown), such as a potentiometer, for adjusting the light intensity as desired or needed. For instance, the light source 210 may include a meter operable to produce light of a suitable intensity and wavelength for use in monitoring the test subject 180. The light source 210 may be fabricated as a light emitting diode (LED) that emits light when connected in a circuit. The light source 210 may also include other circuitry or components for producing light.

The optical emitting waveguide 220 is operable to direct light 225 from the light source 210 onto the test subject 180, or onto a biological substrate of the test subject 180. The optical emitting waveguide 220 may be fabricated as one of the bristle waveguides 215, including a structure such as a light guide, a fiber optic, a light pipe, or other suitable structure operable to direct light 225 from the light source 210 onto the test subject 180. The optical emitting waveguide 220 may also be fabricated to have a suitable length, width or other dimension as needed or desired.

The toothbrush 205 also includes at least one optical receiving waveguide 230 operable to receive or guide light 235 back from the test subject 180, or back from a biological substrate of the test subject 180. The optical receiving waveguide 230 may also be fabricated as a light guide, fiber optic, bristle waveguide, light pipe, or other suitable structure operable to receive or guide light 235 back from the test subject 180, or back from a biological substrate of the test subject 180. The optical receiving waveguide 230 may be fabricated to have a suitable length, width and other dimension as needed or desired.

The optical receiving waveguide 230 is further operable to guide the light 235 from the test subject 180 to a sensor 240. The sensor 240 is operable to detect the light 235 received through the optical receiving waveguide 230. The sensor 240 may include, for instance, at least one of a photodiode, a charge-coupled device (CCD), a photodetector, or other photosensitive element operable to detect the light 235 received by the optical receiving waveguide 230.

The toothbrush 205 further includes a logic component 250 operable to analyze the light 235 detected by the sensors 240. The logic component 250 may include circuitry operable to, for instance, analyze fluorescence of the light 235. The logic component 250 may, for instance, also include circuitry operable to perform one or more logic or arithmetic functions for analyzing the fluorescence and intensity of the light 235 detected by the sensor 240.

The toothbrush 205 also includes an output component 260 operable to convey information from the logic component 250 to a user, such as a user of the toothbrush 205. The output component 260 may include at least one of a visual display and an audible component operable to convey the information to a user. In addition to the output component 260, the toothbrush 205 also includes a housing 270. The housing 270 may be fabricated to contain the light source 210, the sensor 240, the logic component 250, and the output component 260. In addition, the housing 270 may be fabricated out of a synthetic material, such as a plastic or a polymer. The housing 270 may also be fabricated out of a composite of one or more polymers, synthetic materials or alloys.

In addition, the optical emitting waveguide 220 and the optical receiving waveguide 230, in addition to the other bristle waveguides 215, may each extend from a location inside of the housing 270 to a location outside of housing 270. Although the housing 270 is shown in FIG. 2A as having a substantially elongated shape, the housing 270 may have another reasonably suitable shape for function or decorative purposes.

According to one example of the operation of the toothbrush 205, the toothbrush 205 may contain an additional component (not shown) for cutting the subject's gums to obtain a blood sample while brushing. A sample of the subject's blood may thus be obtained in an invasive manner, such as by cutting the gums, or by using another suitable invasive procedure. Alternatively, a blood sample may be obtained in a substantially non-invasive manner, such as by brushing the subject's teeth with the toothbrush 205 such that a blood sample is extracted from around the person's gums because of the brushing action with the bristle waveguides 215. In this example, the bristle waveguides 215 may be configured to cut the person's gums in a minimally invasive manner.

A blood sample obtained either in an invasive or non-invasive manner may be used to provide information about the person's health. For instance, diagnostic tests, analytical tests and other suitable measurements may be performed using the blood sample, or using one or more components of the blood sample, to provide information about the person's health. Alternatively, if a saliva sample is taken, the presence of blood in the saliva sample may be used to analyze for the presence of gum disease. Other health-related conditions, such as the presence of gingivitis, may also be determined by analyzing the person's blood sample. The presence and concentration of gum disease bacteria or other pathogens may also be detected and measured using the person's blood sample or saliva sample.

Although not shown, the toothbrush 205 may also include one or more analytical components operable to generate a profile of a person's teeth based on detected bending of the bristle waveguides 215. More particularly, the bending of a bristle waveguide 215 may be detected through detection and correlation of the amount of light that passes through the bristle waveguide 215. The percentage of light that passes through a bristle waveguide 215 depends at least on the angle at which the light enters the bristle waveguide 215 and the total internal reflection of the light within the bristle waveguide 215. If a bristle waveguide 215 bends, for instance, during a brushing operation, the bending will affect the percentage of light that is transmitted through the bristle waveguide 215. The degree of bending of the bristle waveguide 215 may also be calculated. By dynamically measuring the bending of one or more bristle waveguides 215 as the toothbrush 205 moves along a person's teeth, information may be obtained about the state of health of the person's teeth. For instance, a profile of the person's teeth may be generated based on bending of the bristle waveguides 215 along an outer surface of the teeth due to cavities, abrasion, or teeth misalignment.

The toothbrush 205 may also include electronics, including circuitry, which may operate in conjunction with the logic component 250, operable for analyzing a blood sample collected from the subject for a suitable biological, medical or other healthcare-related purpose. For instance, using the toothbrush 205, a blood sample may be analyzed for one or more of blood glucose level, blood oxygen level, and the presence of other bloodborne factors or agents that may indicate one or more conditions pertaining to the subject's health. Moreover, a temperature gauge (not shown) may also be incorporated in the toothbrush 205, in order to monitor the subject's temperature.

In accordance with another example, a saliva sample may also be obtained from the subject, for instance, in a non-invasive manner by placing the toothbrush 205 in the subject's mouth. The toothbrush 205 may, for instance, include one or more capillaries, in addition to the bristle waveguides 215, operable to draw out a saliva sample from the subject's mouth. The toothbrush 205 may also include electronics, including circuitry, which may operate in conjunction with the logic component 250, operable for analyzing the saliva sample collected from the subject for a suitable biological, medical or other healthcare-related purpose. For instance, additional electronics may be incorporated in the toothbrush 205 for testing the saliva sample for cortisol, alpha-amylase, or one or more types of immunoglobulins. The test results may be used, for example, to provide information about the subject's health. In another example, a sample of the subject's sweat or other bodily fluid may also be obtained in a non-invasive manner, to provide information about the subject's health.

According to another example, a toothpaste formulation or other suitable chemical formulation may be used in conjunction with the toothbrush 205. The chemical formulation may be created to have different formulations, depending on the needs or requirements of a user. For instance, if a test of a saliva sample requires the use of one or more biochemical agents or reagents, such as an antibody or other agent for chemical detection, such agents may be provided in a chemical formulation as needed or desired. In one example, the toothbrush 205 may be used to apply a toothpaste formulation or other suitable chemical formulation to the teeth or other area of the test subject 180. The chemical formulation may include a formulation or composition that contains a chemical or reagent solution for performing a specific diagnostic test. When the chemical formulation contacts saliva or other blood components, such as a saliva sample obtained from the test subject 180, the chemical formulation may cause a reaction to occur. The reaction may have, as its end-product, a substance that may be optically detected by the toothbrush 205, as described in detail above. The light detected may be analyzed by the logic component 250, and information based on the analyzed light may be conveyed using the output component 260. The toothbrush 205 may thus be used to apply a toothpaste, chemical agent, or other chemical formulation with a biological substrate, such as a saliva sample. The biological substrate may then react with the toothpaste, chemical agent, or other chemical formulation, and a product of the reaction may be optically detected by the toothbrush 205. The toothbrush 205 may also be designed with rotating bristles 215 or otherwise movable bristles 215, which may also be used in conjunction with a toothpaste formation or other suitable chemical formulation.

Although the device 205 is shown in FIG. 2A as a toothbrush, the device 205 may alternatively be constructed as another suitable type of brush, such as a hairbrush. A hairbrush, in a manner similar to the toothbrush, may have one or more bristle waveguides 215 and may also be constructed in accordance with the other components shown and described above, with reference to FIG. 2A. The hairbrush may thus also be used to monitor the test subject 180, for instance, by monitoring the scalp of the test subject 180. In addition, the device 205 may also be fabricated as another type of instrument suitable for insertion in a bodily cavity, such as insertion in the ear or nose for monitoring the health of a person. Thus, the device 205 may be used for monitoring, testing and diagnosis of the test subject 180.

Figure 2B:
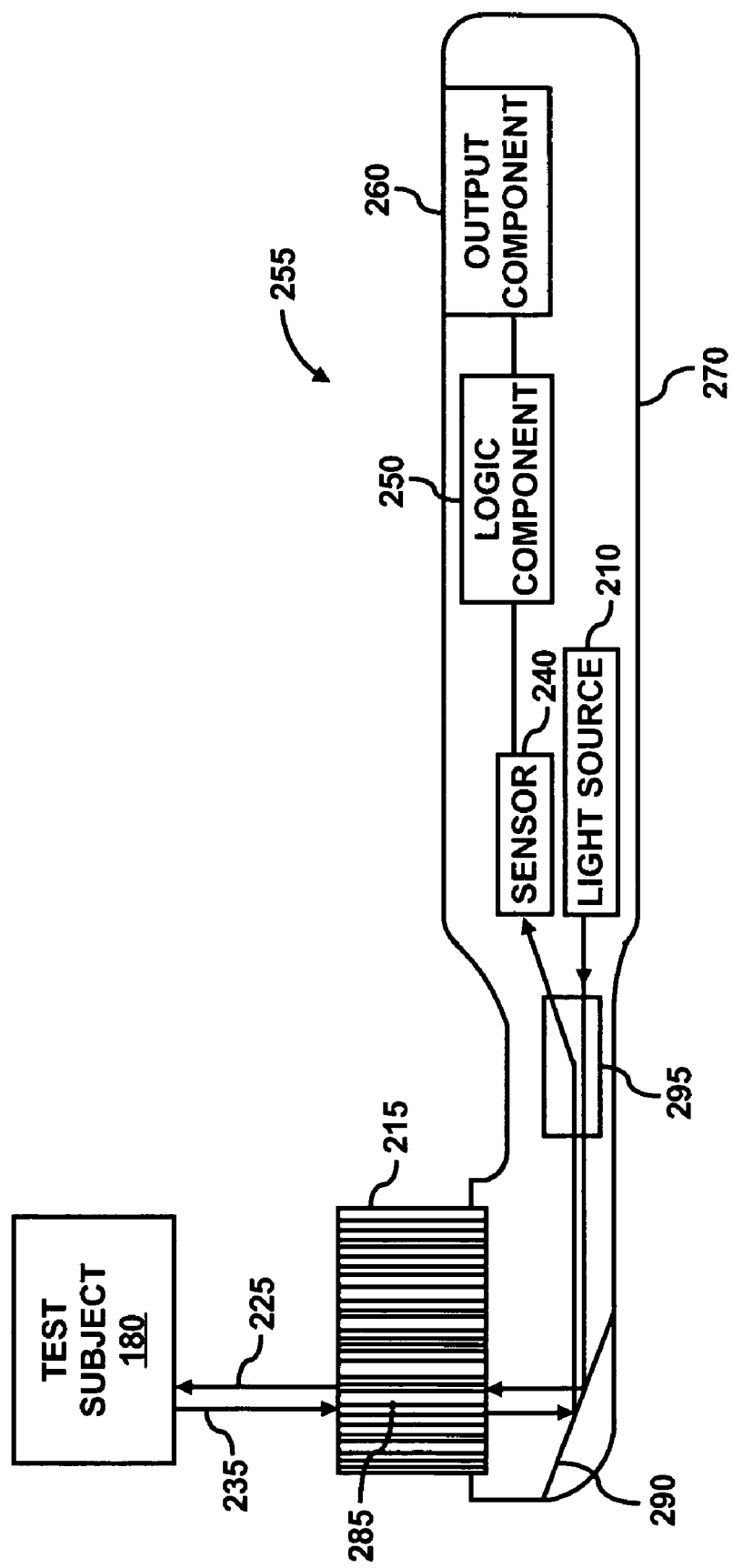
FIG. 2B shows a device for monitoring a test subject, where the device comprises at least one optical waveguide, and a light-separating component, according to an embodiment.

Referring to FIG. 2B, a toothbrush 255 may include at least one optical waveguide 285. Identical numbered features, as described above with reference to the toothbrush 205 shown in FIG. 2A, also apply to the toothbrush 255 shown in FIG. 2B, and are thus not described in great detail herein.

The optical waveguide 285 is operable both to direct the light 225 from the light source 210 onto the test subject 180 and to receive the light 235 directed onto, and guided back from, the test subject 180. The optical waveguide 285 is thus operable both as a light input guide and as a light output guide. The optical waveguide 285 may include, but is not limited to, a fiber optic, a light pipe, a light guide, a bristle waveguide, or other suitable structure operable both as a light input guide and a light output guide. Furthermore, the optical waveguide 285 may form a bristle, in addition to the bristle waveguides 215, where at least a portion of the optical waveguide 285 extends outside of the housing 270.

As further shown in FIG. 2B, a reflective material 290 and a light-separating component 295 may be inserted between the optical waveguide 285 and the light source 210 and the sensor 240. The reflective material 290 may include a mirror or other suitable reflection component. Although the reflective material 290 is shown in one orientation and position within the housing 270, the reflective material 290 may also be located in another suitable orientation and position within the housing 270. Although not shown, one or more other components, such as other light-reflective components, may also be used for operation with the toothbrush 255.

Again referring to FIG. 2B, the light-separating component 295 may be used in conjunction with the at least one optical waveguide 285. The light-separating component 295 is operable to at least partially separate the light 225 that is directed onto the test subject 180 from the light 235 that is received back from the test subject 180. The light-separating component 295 is thus operable to at least partially separate the transmitted light 225 from the received light 235 guided through the optical waveguide 285.

The light-separating component 295 may include, for example, a beamsplitter, a waveguide light-splitter, a polarizing cube, and the like. Examples of suitable beamsplitters include, but are not limited to, broadband plate beamsplitters, laser cube beamsplitters, polarizing cube beamsplitters, beam samplers, metallized plate beamsplitters, metallized cube beamsplitters, and the like. The light-separating component 295 may thus use polarization to separate the transmitted light 225 from the received light 235 guided through the optical waveguide 285. In addition, the light-separating component 295 is operable to both transmit light to the optical waveguide 285 and receive light from the optical waveguide 285.

The light-separating component 295 may achieve at least partial separation of the transmitted light 225 from the received light 235 guided through the optical waveguide 285. Examples of a light-separating component 295 that may achieve partial separation of the transmitted light 225 from the received light 235 include a 50/50 beam splitter and a Y-coupled optic fiber. Alternatively, the light-separating component 295 may achieve 100 percent complete, or substantially complete, separation of the transmitted light 225 from the received light 235 guided through the optical waveguide 285. An example of a light-separating component 295 that may achieve complete separation of the transmitted light 225 from the received light 235 includes a polarizing beamsplitter with a ¼ wave plate.

In one example, the light transmitted from the light source 210 is transmitted through the light-separating component 295 and to the reflective material 290. Upon luminating the reflective material 290, the light is transmitted to the optical waveguide 285, where the light 225 is directed onto the test subject 180. The optical waveguide 285 also operates to guide the light 235 back from the test subject 180. The light 235 guided back from the test subject 180 is transmitted from the optical waveguide 285 to the reflective materials 290. The light 235 is directed to the light-separating component 295 from the reflective material 290. The light-separating component 295 operates to direct the received light 235 to the sensor 240.

Figure 2C:
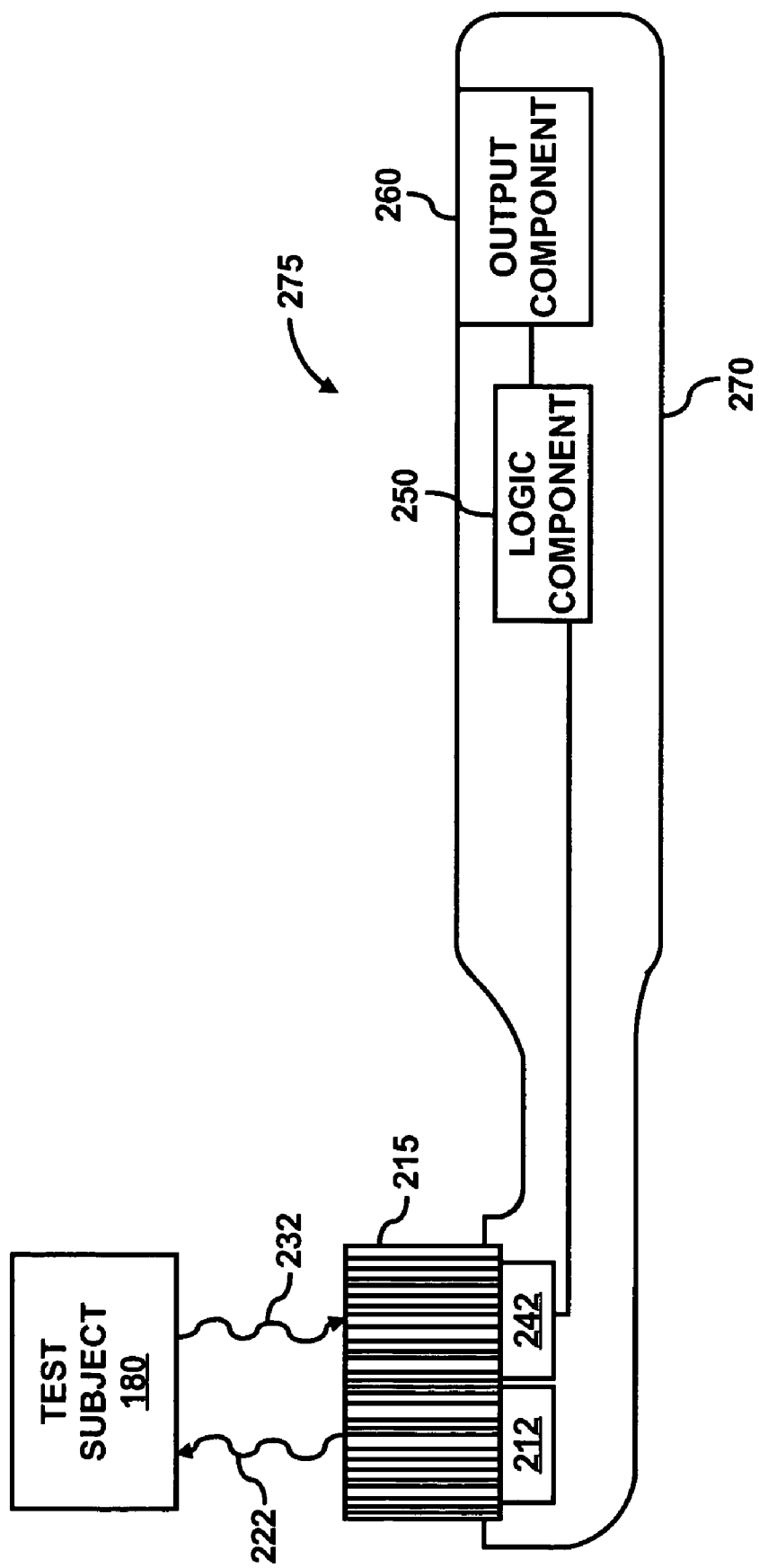
FIG. 2C shows a device for monitoring a test subject, where the device comprises an ultrasonic source and detector, according to an embodiment.

Referring to FIG. 2C, a toothbrush 275 is shown for monitoring the test subject 180. Identical numbered features, as described above with reference to the toothbrush 205 shown in FIG. 2A, also apply to the toothbrush 275 shown in FIG. 2C, and are thus not described in great detail herein. The toothbrush 275 comprises an ultrasound source 212 and an ultrasound detector 242. The ultrasound source 212 may transmit acoustic or ultrasonic waves at a desired frequency onto the test subject 180. Although the ultrasound source 212 is shown at a particular location and orientation inside the housing 270, the ultrasound source 212 may also be located at another suitable location inside the housing 270. The ultrasound source 212 may emit a plurality of ultrasonic waves 222. The ultrasound source 212 may emit the ultrasonic waves 222 at a suitable frequency and, in addition, the frequency emitted may be adjusted as needed or desired. As shown in FIG. 2C, the ultrasonic waves 222 may pass or propagate through the bristle waveguides 215 and onto the test subject 180. Alteratively, the ultrasonic waves 222 may pass or propagate through another surface of the toothbrush 275 and onto the test subject 180.

Referring again to FIG. 2C, the ultrasonic waves may contact the test subject 180. The test subject 180 may include, for instance, a person's teeth. As the ultrasonic waves 222 contact the test subject 180, the waves 222 rebound or bounce back from the test subject 180. Thus, upon propagation of the acoustic or ultrasonic waves from the toothbrush 275, the acoustic or ultrasonic waves may contact and then rebound back from the person's teeth.

The ultrasound detector 242 may receive the rebounded ultrasonic waves 232. Information regarding the detected ultrasonic waves 232 may be obtained upon analysis by the logic component 250. The logic component 250 may include circuitry or other suitable processing components operable to analyze the frequency and other parameters of the detected ultrasonic waves 232. The detected ultrasonic waves 232 may be analyzed to provide information about the health of the test subject, such as whether the test subject 180 has cavities or other dental conditions. In addition, the analyzed information may be conveyed via the output component 260.

The toothbrush 275 may also operate as a sonophoresis device, such as a sonophoresis actuator, for use in cavity detection or for other diagnostic purposes. The use of sonophoresis or ultrasound may thus be incorporated within the toothbrush 275, such that cavities and other health or dental-related conditions may be detected.

Figure 3A:
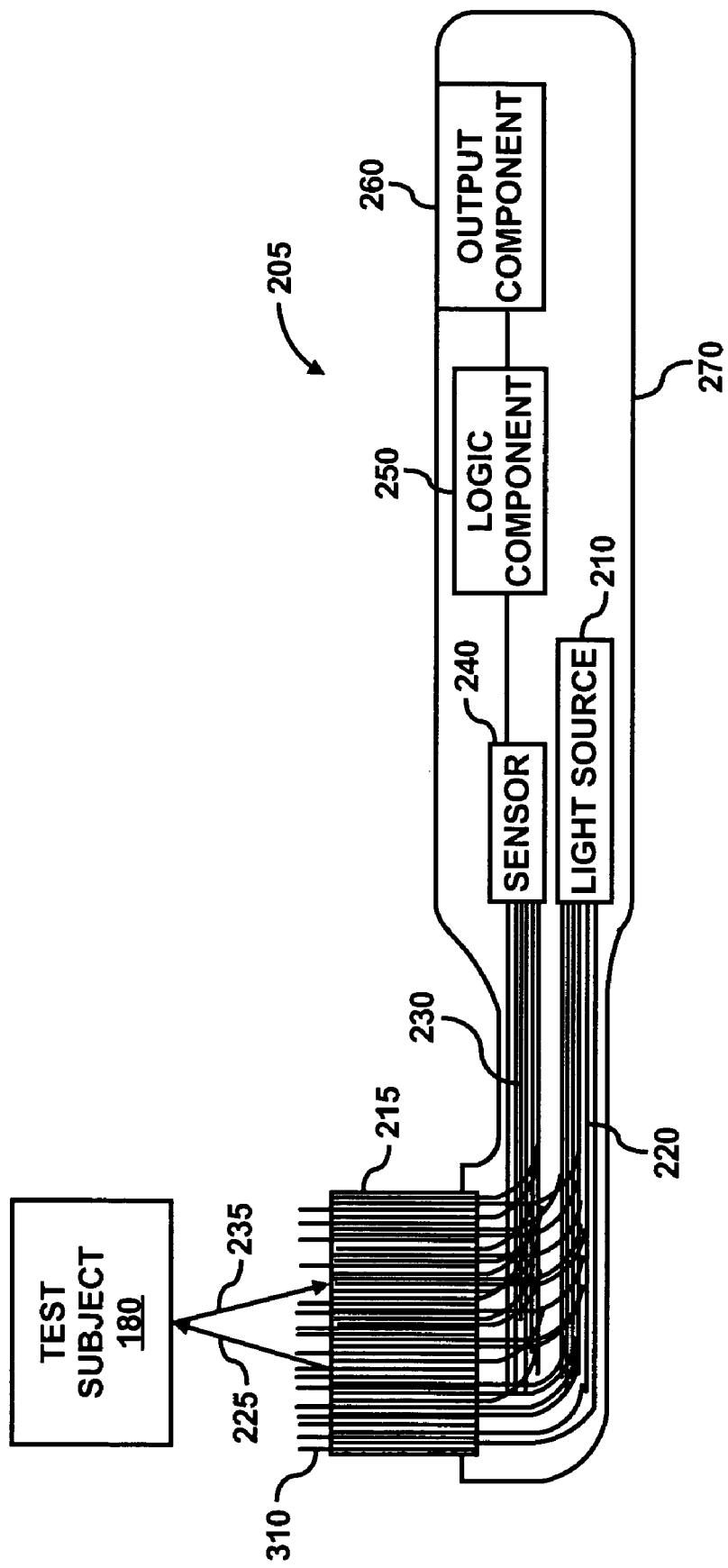
FIG. 3A shows a device for monitoring a test subject, where the device comprises a plurality of bristle waveguides of different lengths, according to an embodiment.

Referring to FIG. 3A, the device 205 is illustrated as comprising another set of bristles 310 in addition to the plurality of bristle waveguides 215. In addition to the optical emitting wavelength 220 and the optical receiving waveguide 230, which may each extend a first distance from the housing 270, the other set of bristles 310 may also extend a second distance from the housing 270. The second distance is longer than the first distance, such that the bristles 310 extend further from the housing 270 than the bristle waveguides 215.

Figure 3B:
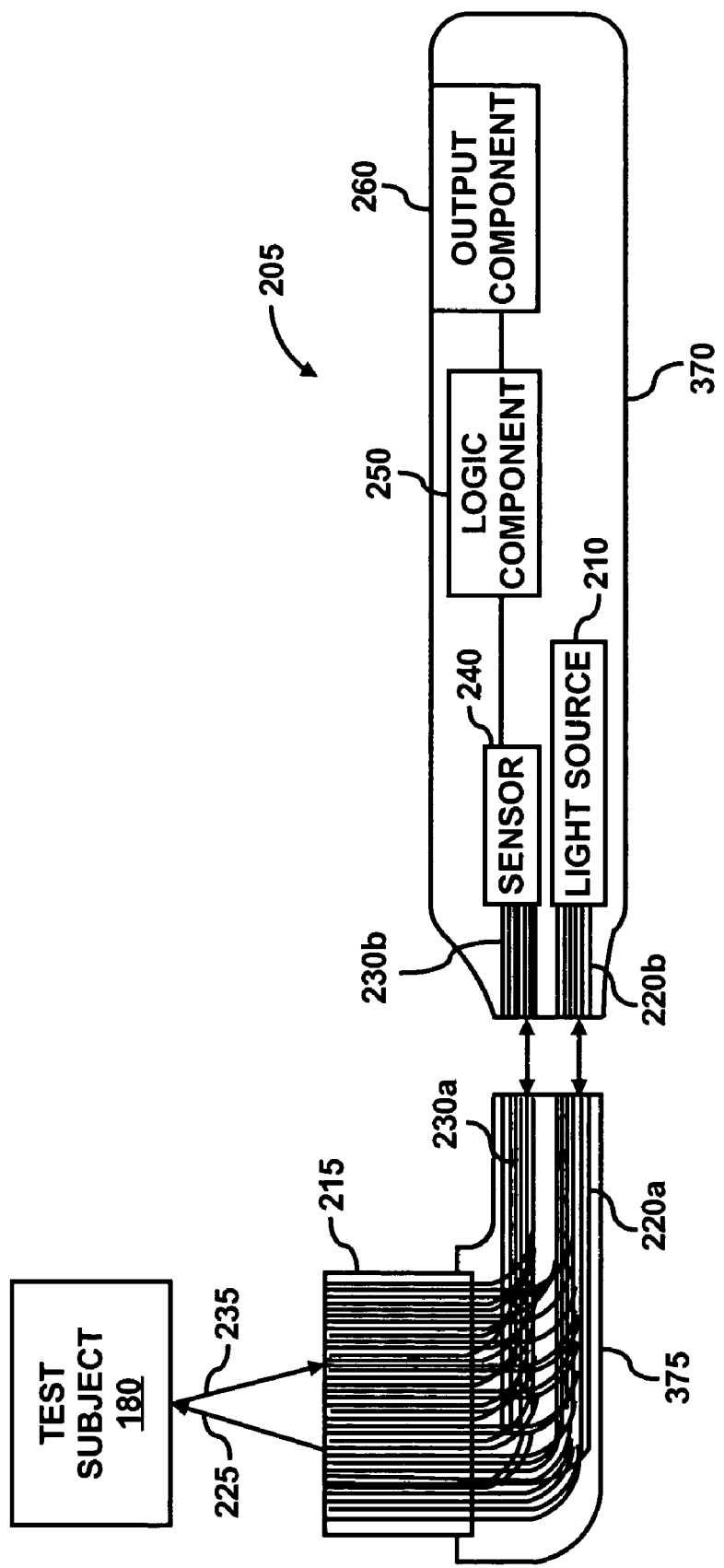
FIG. 3B shows a device for monitoring a test subject, where the device comprises detachable components, according to an embodiment.

Referring to FIG. 3B, a toothbrush 205 is shown as described above in detail, with reference to FIGS. 2 and 3A. In addition to the features as shown and described above, the toothbrush 205 also contains a base portion 370 and a detachable head portion 375. The detachable head portion 375 may be detached from, and reattached to, the base portion 370 through any reasonably suitable fastening mechanisms. The fastening mechanisms may include, for instance, a screw mechanism, a snap or other suitable fastener mechanism, a male-female configuration with suitable male-female mating components, etc. Thus, the base portion 370 may be reversibly detached from, and reattached to, the head portion 375. The detachable head portion 375 thus allows for a user to replace an old or worn head portion 375 with a new, disposable head portion. Old or worn bristle waveguides 215 from an old or worn head portion 375 may thus be replaced with new bristle waveguides 215 on a new head portion 375 for attachment to the base portion 370 of the toothbrush 205.

A different type of head portion, such as a head portion containing a different type of bristle waveguides 215, may be used for attaching to the base portion 370, for suitable monitoring of the test subject 180. With the detachable configuration shown in FIG. 3B, an optical waveguide segment 220a may be maneuvered away from and toward an optical waveguide segment 220b to thereby enable light from the light source 210 to be directed to the test subject 180. In a similar manner, an optical waveguide segment 230a may be maneuvered away from and toward an optical waveguide segment 230b to thereby enable light from the test subject 180 to be directed to the sensor 240. In this regard, various detachable head portions 375 may be employed with a single base portion 370. Thus, for instance, the toothbrush 205 depicted in FIG. 3B may be used on a number of different test subjects 180.

Figure 4:
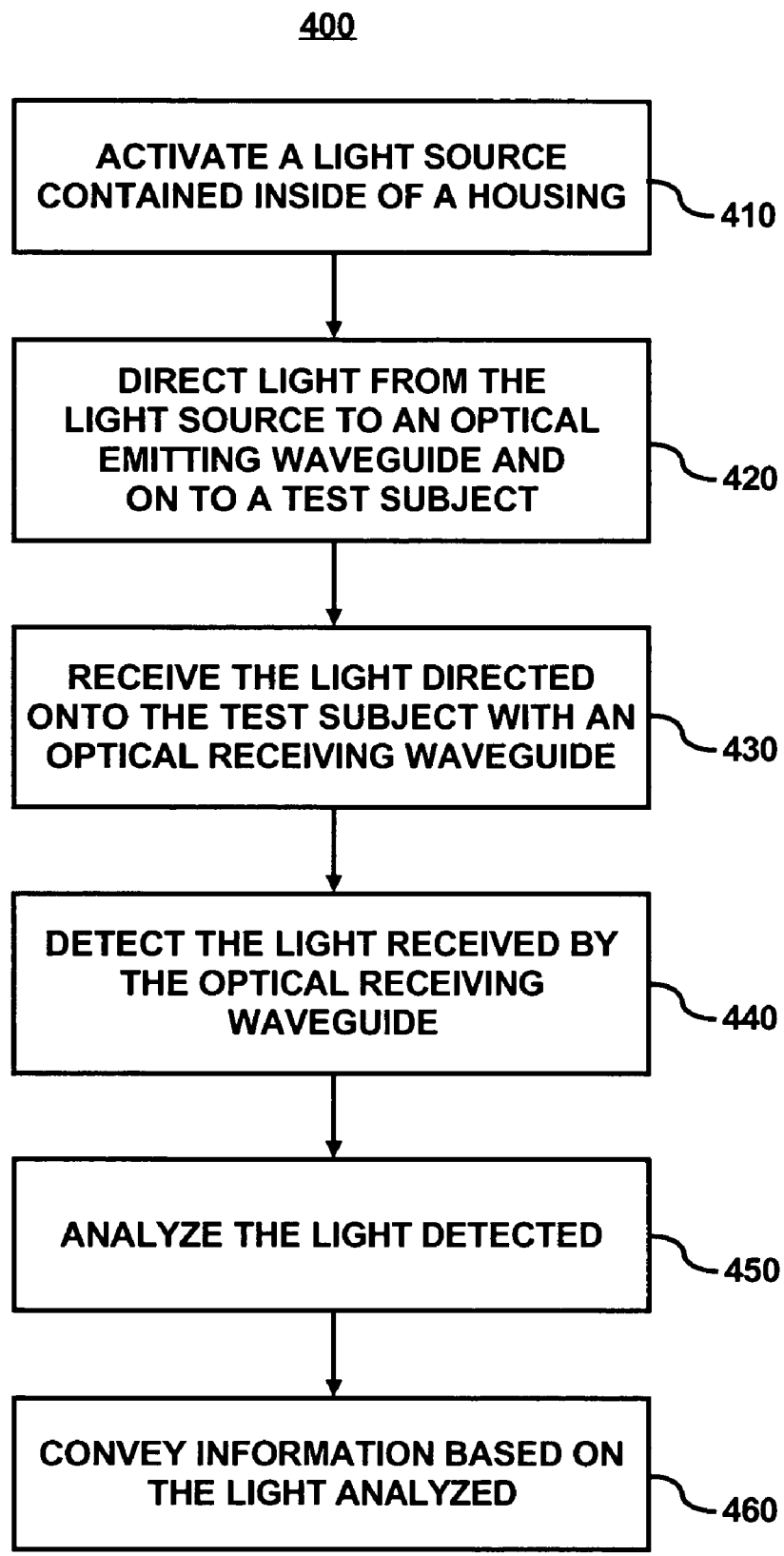
FIG. 4 shows a flowchart for conveying information based on detecting and analyzing light received by an optical receiving waveguide, according to an embodiment.

Referring to FIG. 4, a flowchart 400 is shown illustrating a method of monitoring the test subject 180. The method illustrated in the flowchart 400 may be performed through use of, for instance, any of the devices 105, 205 depicted in FIGS. 1, 2A, 2B, 3A, and 3B.

At step 410, the light source 210 contained inside of the housing 270 is activated. At step 420, light from the light source 210 is directed to the optical emitting waveguide 220 and onto the test subject 180, wherein the optical emitting waveguide 220 forms one of the bristle waveguides 215 extending outside of the housing 270. At step 430, the light directed onto the test subject 180 is received or guided back with the optical receiving waveguide 230, wherein the optical receiving waveguide 230 also forms one of the bristle waveguides 215 extending outside of the housing 270. At step 440, the light 235 received by the optical receiving waveguide 230 is detected by the sensor 240. At step 450, the light detected by the sensor 240 is analyzed, such as by the logic component 250. At step 460, the information obtained, and based on the light analyzed, is conveyed to a user through the output component 260.

Figure 5:
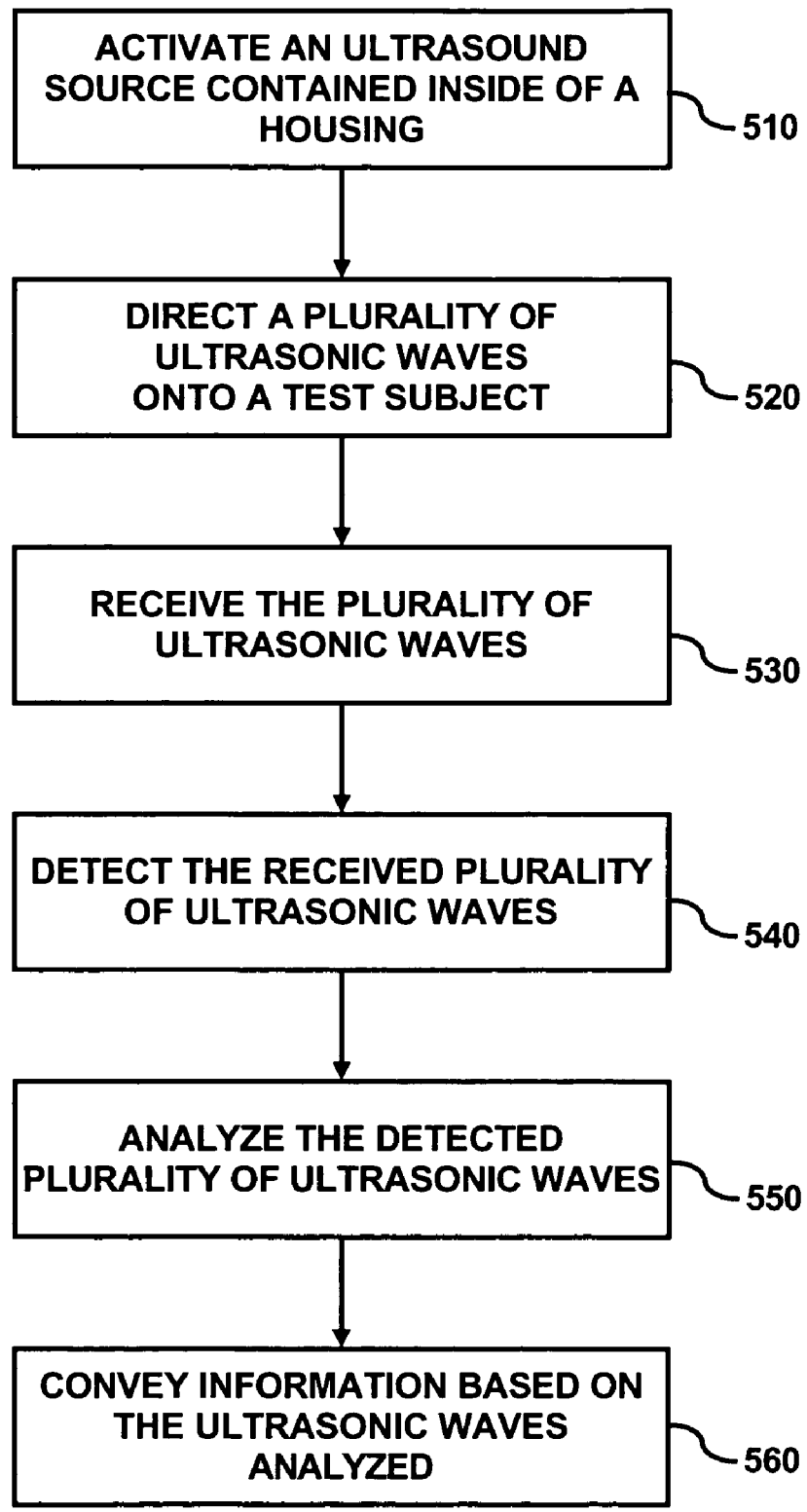
FIG. 5 shows a flowchart for conveying information based on detecting and analyzing a plurality of ultrasonic waves, according to an embodiment.

Referring to FIG. 5, a flowchart 500 is shown illustrating a method of monitoring the test subject 180 by a plurality of ultrasonic waves. The method illustrated in the flowchart 500 may be performed through use of, for instance, the device 275 depicted in FIG. 2C.

At step 510, the ultrasound source 212 contained inside of the housing 270 is activated. The ultrasound source 212 may be activated at a suitable frequency, as needed or desired. At step 520, a plurality of ultrasonic waves 222 from the ultrasound source 212 is directed onto the test subject 180. Propagation of the ultrasonic waves 222 is described in further detail above, with reference to FIG. 2C. The plurality of ultrasonic waves 222 may rebound or bounce back from the test subject 180. At step 530, the rebounded plurality of ultrasonic waves 232 are received. At step 540, the received plurality of ultrasonic waves 232 are detected, for instance, by the ultrasound detector 242. At step 550, the detected plurality of ultrasonic waves 232 are analyzed, for instance, by the logic component 250. At step 560, information is conveyed based on the plurality of ultrasonic waves 232 that are analyzed. The information may be conveyed, for instance, by the output component 260.

What has been described and illustrated herein are embodiments along with some variations. While the embodiments have been described with reference to examples, those skilled in the art will be able to make various modifications to the described embodiments without departing from the true spirit and scope. The terms and descriptions used herein are set forth by way of illustration only and are not meant as limitations. In particular, although the methods have been described by examples, steps of the methods may be performed in different orders than illustrated or simultaneously. Those skilled in the art will recognize that these and other variations are possible within the spirit and scope as defined in the following claims and their equivalents.

What is claimed is:

1. A device for monitoring a test subject, comprising:
   a light source configured to emit light;
   a plurality of optical waveguides configured for directing the light emitted from the light source onto a biological substrate to be reflected off of the biological substrate and for receiving the light reflected off the biological substrate;
   a sensor operable to detect the reflected light received by the at least one optical waveguide;
   a logic component operable to analyze the light detected by the sensor;
   an output component operable to convey information from the logic component to a user of the device; and
   a housing containing the light source, the sensor, the logic component, and the output component, wherein the plurality of optical waveguides form bristles extending outside of the housing to directly receive the reflected light.

2. The device of claim 1, wherein the sensor comprises at least one of a photodiode, a CCD device, and a photodetector.

3. The device of claim 1, wherein the sensor is further operable to analyze a spectral content of the light detected by the sensor by at least one of a grating, a prism, and an interferometer.

4. The device of claim 1, wherein the biological substrate comprises at least one of saliva and blood from a test subject.

5. The device of claim 1, wherein the bristles have at least one chemical agent disposed thereon, such that the at least one chemical agent is configured to be combined with the biological substrate for detecting a reaction with the biological substrate.

6. The device of claim 1, wherein the output component comprises at least one of a visual display and an audible component operable to convey the information to the user.

7. The device of claim 1, wherein the device comprises at least one of a toothbrush and a hairbrush, wherein the bristles are arranged in a substantially parallel configuration with each other.

8. The device of claim 1, wherein the plurality of optical waveguides comprises a plurality of optical fibers extending from a location inside of the housing to a location outside of the housing.

9. The device of claim 1, wherein the bristles comprise substantially hollow capillaries having openings in a region of the bristles located outside of the housing such that the bristles are configured to allow at least one of blood and saliva to enter the bristles through the openings.

10. The device of claim 1, wherein a portion of the plurality of one optical waveguides are detachable from the housing.

11. The device of claim 1, further comprising:
    at least one light-separating component operable to at least partially separate the light directed onto the biological substrate from the light received.

12. The device of claim 11, wherein the at least one light-separation component comprises at least one of a beamsplitter, a waveguide light-splitter and a polarizing cube.

13. The device of claim 1, wherein the sensor, the logic component, and the plurality of optical waveguides are together operable for non-invasive monitoring, testing and diagnosis of a test subject.

14. The device of claim 13, wherein at least one of a toothpaste formulation, a chemical agent, and a chemical formulation is provided on the bristles for the non-invasive monitoring, testing and diagnosis of the test subject.

15. The device of claim 1, wherein the bristles formed by the plurality of optical waveguides extend a first distance from the housing, said device further comprising another set of bristles extending a second distance from the housing, wherein the second distance is longer than the first distance.

16. A method of monitoring a test subject, comprising:
    activating a light source contained inside of a housing to emit light;
    directing the light from the light source to at least one optical waveguide and onto the test subject to reflect the light off of the test subject, wherein the at least one optical waveguide forms at least one bristle extending outside of the housing;
    receiving the light reflected off the test subject with another one optical waveguide, wherein the another optical waveguide forms another bristle extending outside of the housing to directly receive the light reflected off of the biological substrate and, wherein the at least one bristle and the another bristle are arranged in a substantially parallel configuration;
    detecting the reflected light received by the another optical waveguide;
    analyzing the light detected; and
    conveying information based on the light analyzed.

17. The method of claim 16, wherein analyzing the light detected further comprises:
    analyzing the fluorescence of the light detected; and
    determining information about the test subject based on the fluorescence analyzed.

18. The method of claim 16, wherein the test subject has at least one selected from hair and teeth and the method further comprises at least one selected from:
    brushing the hair of the test subject with the at least one bristle or the another bristle and
    brushing the teeth of the test subject with the at least one bristle or the another bristle.

19. The method of claim 16, wherein the another bristle comprises a substantially hollow capillary having an opening therein, and, wherein the method further comprises:
    receiving at least one of blood and saliva through an opening in the another bristle.

20. The method of claim 16, wherein conveying information based on the light analyzed further comprises conveying information with at least one of a visual display and an audible component for a user.

21. The method of claim 16, further comprising:
    applying at least one chemical formulation to an area of the test subject; and
    analyzing the light detected in the presence of the at least one chemical formulation.

22. The method of claim 16, further comprising detaching the housing from the at least one optical waveguide, such that the at least one optical waveguide may be replaced.

23. The method of claim 16, wherein conveying the information further comprises conveying the information for at least one of monitoring, testing, profiling and diagnosis of the test subject.

24. A system for monitoring a test subject, comprising:
means for shining light;
means for directing light onto the test subject to reflect the light off of the test subject;
means for receiving the light reflected off of the test subject;
means for detecting the reflected light received;
means for analyzing the light detected; and
means for outputting information based on analysis of the reflected light detected, wherein the means for detecting the reflected light received, the means for analyzing the reflected light detected, and the means for outputting the information are contained within a housing, further wherein the means for directing the light and the means for receiving the reflected light from bristles extending from a location inside of the housing to a location outside of the housing such that the means for receiving the light is configured to directly received the light reflected off of the test subject.

25. The system of claim 24, further comprising means for detaching the housing from the means for directing the light and the means for receiving the reflected light.

* * * * *

UNITED STATES PATENT AND TRADEMARK OFFICE
CERTIFICATE OF CORRECTION

PATENT NO. : 7,386,333 B1
APPLICATION NO. : 11/117974
DATED : June 10, 2008
INVENTOR(S) : Henryk Birecki et al.

It is certified that error appears in the above-identified patent and that said Letters Patent is hereby corrected as shown below:

In column 1, line 12, delete "blond" and insert -- blood --, therefor.

In column 1, line 44, delete "senor" and insert -- sensor --, therefor.

In column 3, line 22, delete "280" and insert -- 180 --, therefor.

In column 3, line 53, delete "senor" and insert -- sensor --, therefor.

In column 5, line 66, after "outside of" insert -- the --.

In column 7, line 47, delete "formation" and insert -- formulation --, therefor.

In column 8, line 17, delete "reflection" and insert -- reflective --, therefor.

In column 9, line 54, delete "wavelength" and insert -- waveguide --, therefor.

In column 11, line 66, in Claim 10, delete "one" before "optical".

In column 12, line 5, in Claim 12, delete "separation" and insert -- separating --, therefor.

In column 12, line 29, in Claim 16, delete "one" before "optical".

UNITED STATES PATENT AND TRADEMARK OFFICE
CERTIFICATE OF CORRECTION

PATENT NO. : 7,386,333 B1
APPLICATION NO. : 11/117974
DATED : June 10, 2008
INVENTOR(S) : Henryk Birecki et al.

It is certified that error appears in the above-identified patent and that said Letters Patent is hereby corrected as shown below:

In column 12, line 53, in Claim 19, after "therein" delete ",".

In column 14, line 5, in Claim 24, delete "from" and insert -- form --, therefor.

In column 14, line 8, in Claim 24, delete "received" and insert -- receive --, therefor.

Signed and Sealed this

Fourteenth Day of April, 2009

JOHN DOLL
*Acting Director of the United States Patent and Trademark Office*